United States Patent [19]

Lee

[11] 4,146,625

[45] Mar. 27, 1979

[54] QUINOLONECARBOXYLIC ACIDS FOR CONTROL OF BACTERIAL DISEASES IN PLANTS

[75] Inventor: Kyu T. Lee, Wilmington, Del.

[73] Assignee: E. I. Du Pont de Nemours and Company, Wilmington, Del.

[21] Appl. No.: 877,463

[22] Filed: Feb. 13, 1978

Related U.S. Application Data

[63] Continuation-in-part of Ser. No. 706,010, Jul. 16, 1976, abandoned.

[51] Int. Cl.$^2$ .................... A01N 9/22; C07D 215/00; C07D 215/14; C07D 215/58
[52] U.S. Cl. .................................... 424/258; 546/156
[58] Field of Search .................. 424/258; 260/283 S, 260/287 AN, 286 R, 270 C, 286 Q

[56] References Cited

U.S. PATENT DOCUMENTS

| | | | |
|---|---|---|---|
| 3,849,421 | 11/1974 | Nakagome et al. | 260/283 S |
| 3,924,042 | 12/1975 | Gerster | 424/258 |
| 3,966,743 | 6/1976 | Berger et al. | 424/258 |

FOREIGN PATENT DOCUMENTS

| | | | |
|---|---|---|---|
| 4410549 | 5/1969 | Japan. | |
| 4747394 | 11/1972 | Japan | 260/283 S |
| 830832 | 3/1960 | United Kingdom. | |

*Primary Examiner*—Allen J. Robinson

[57] ABSTRACT

Quinolonecarboxylic acids, such as 6-fluoro-1,4-dihydro-8-methyl-4-oxo-1-(2,2,2-trifluoroethyl)-3-quinolonecarboxylic acid, ethyl ester, useful for control of certain bacterial plant diseases, such as fire blight of apple, pear and soft rot of potato, and gall formation on herbaceous and woody plants.

37 Claims, No Drawings

QUINOLONECARBOXYLIC ACIDS FOR CONTROL OF BACTERIAL DISEASES IN PLANTS

RELATED APPLICATION

This is a continuation-in-part of Ser. No. 706,010 filed July 16, 1976 now abandoned.

BACKGROUND OF THE INVENTION

This invention relates to quinolonecarboxylic acid antibacterials for plants.

Gerster, J. F., in U.S. Pat. No. 3,924,042, discloses a method for treatment of plant disease caused by bacteria using a compound of the following formula:

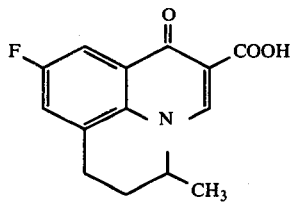

Gerster, J. F., in U.S. Pat. No. 3,917,609 discloses pharmaceutically useful pyrroloquinoline carboxylic acid antibacterials including, among other compounds, those of the following formula:

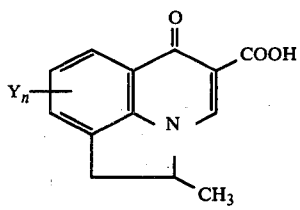

wherein Y can be alkyl, alkoxy, halogen, hydroxyl, nitro, cyano, trifluoromethyl, or amino.

Streptomycin (Agri-Strep®) is the commercial product most widely used for control of fire blight.

The compounds of this invention are superior to both streptomycin and the prior art compound of Gerster, U.S. Pat. No. 3,924,042, for control of fire blight.

SUMMARY OF THE INVENTION

According to this invention there is provided compounds of the following formula, processes for preparing them, horticultural compositions containing them, and methods of using them to control certain plant bacterial diseases.

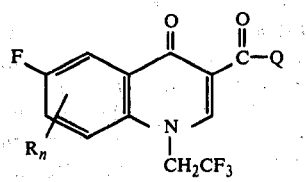

where
R = methyl or fluorine;
n = 0, 1, or 2,
Q = OR$_1$ or SR$_1$; and
R$_1$ = hydrogen, alkyl of 1-8 carbons, 2,2-dimethyl-1-oxopropoxymethyl, or horticulturally-suitable metal, amine, or ammonium salts;

provided when R is fluorine, n is 1.

DETAILED DESCRIPTION OF THE INVENTION

Preferred Compounds

Preferred for their greater biological activity are those compounds where, independently:

(a) n = 1 or 2; or
(b) Q = OR$_1$; or
(c) R$_1$ is hydrogen, alkyl of 1-4 carbons, 2,2-dimethyl-1-oxopropoxymethyl, or horticulturally-suitable metal, amine, or ammonium salts.

More preferred for higher activity are those compounds where n, Q and R$_1$ have the preferred definitions.

Specifically preferred for their outstanding activity are:

(a) 6-fluoro-1,4-dihydro-4-oxo-1-(2,2,2-trifluoroethyl)-3-quinolinecarboxylic acid, (2,2-dimethyl-1-oxopropoxymethyl) ester
(b) 6-fluoro-1,4-dihydro-8-methyl-4-oxo-1-(2,2,2-trifluoroethyl)-3-quinolinecarboxylic acid, ethyl ester
(c) 6-fluoro-1,4-dihydro-8-methyl-4-oxo-1-(2,2,2-trifluoroethyl)-3-quinolinecarboxylic acid
(d) 6-fluoro-1,4-dihydro-7,8-dimethyl-4-oxo-1-(2,2,2-trifluoroethyl)-3-quinolinecarboxylic acid
(e) 6,8-difluoro-1,4-dihydro-4-oxo-1-(2,2,2-trifluoroethyl)-3-quinolinecarboxylic acid
(f) 6,8-difluoro-1,4dihydro-4-oxo-1-(2,2,2-trifluoroethyl)-3-quinolinecarboxylic acid, ethyl ester

SYNTHESIS

The compounds of this invention can be prepared by reacting an appropriately-substituted N-(2,2,2-trifluoroethyl)-aniline (1) with a dialkyl alkoxymethylenemalonate (2) without solvent at 100° to 200° C., preferably 150° to 175° C., for 1 to 24 hours (Equation A). The resulting intermediates (3) are not usually isolated or purified, but cyclized by heating in polyphosphoric acid at 100° to 140° C. for 0.25 to 2 hours, preferably 0.5 to 1 hour (Equation B). The resulting esters (4) are readily purified by recrystallization or chromatography.

Equation A

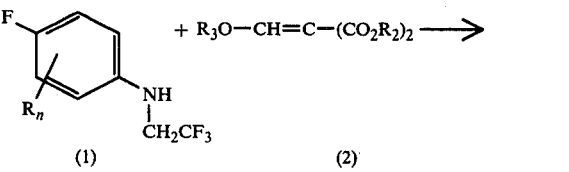

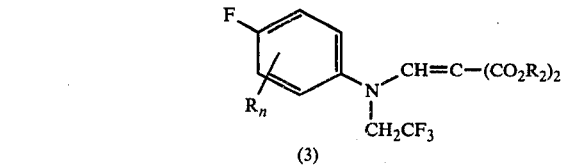

Equation B

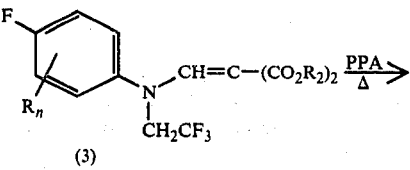

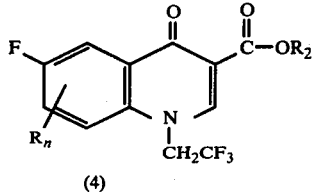

(4)

(where R and n are as defined above, $R_2$ is alkyl of 1 to 4 carbon atoms, and $R_3$ is methyl or ethyl.)

Other carboxylic acid derivatives (where Q is $OR_1$ or $SR_1$) can be prepared from (4) first by hydrolysis in either acid or base (e.g., refluxing 3 hours in 6N hydrochloric acid, or heating 1-2 hours at 90° in 10% sodium hydroxide followed by neutralization) to give the carboxylic acid (5) (Equation C).

Esters and thiol esters of this invention are prepared from (5) by conventional techniques, e.g., by reacting (5) with thionyl chloride, then reacting the intermediate acid chloride with an alcohol or thiol (Equation D).

Equation C

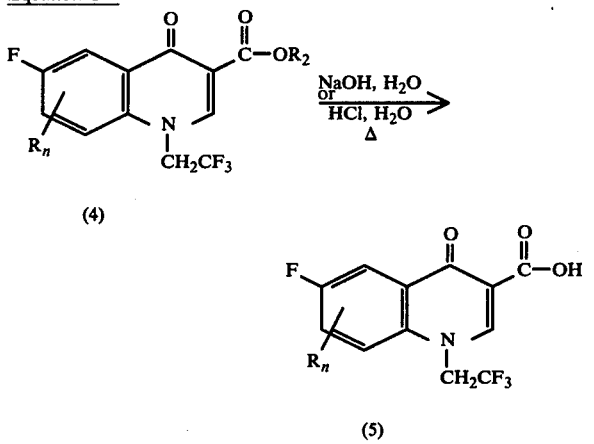

Equation D

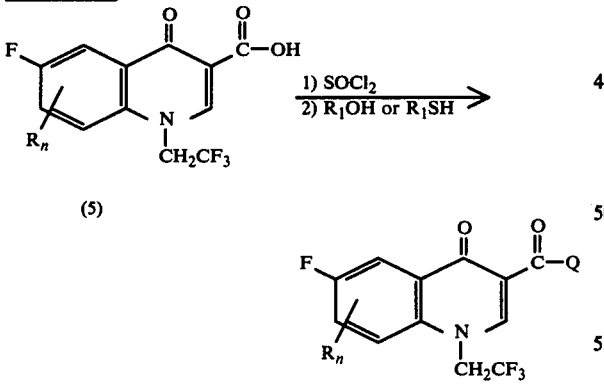

Salts of the free acids are readily prepared by reaction of the acid (5) with a base and evaporation to dryness; the base may be organic or inorganic.

The N-(2,2,2-trifluoroethyl)anilines (1) used are available from the corresponding aniline (6) by first reaction with trifluoroacetic anhydride in an inert solvent such as benzene to give the trifluoroacetanilide (7) which is reduced to the required N-(2,2,2-trifluoroethyl)aniline in high yield with borane (Equations E and F). Borane is commercially available as a complex with tetrahydrofuran, or can be generated in situ from sodium borohydride and boron trifluoride etherate [H. C. Brown et al., J. Am. Chem. Soc., 82, 684 (1960)].

Equation E

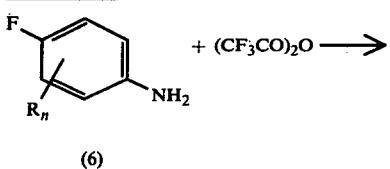

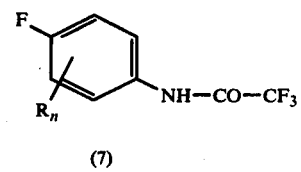

(7)

Equation F

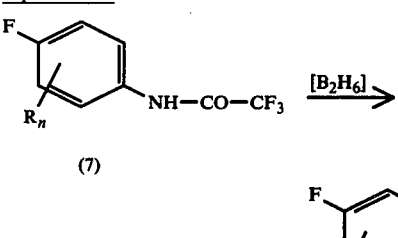

(1)

The fluoroanilines (6) are either commercially available (n = 0) or can be prepared by conventional nitration and reduction of commercially available fluorotoluenes and fluoroxylenes [e.g., G. Valkanas, J. Chem. Soc., 5554 (1963)].

The following examples are provided to further illustrate synthetic methods useful for making the compounds of this invention. Unless otherwise stated, all parts and percentages are by weight and all temperatures are in degrees centigrade.

EXAMPLE 1

A. 4-Fluoro-2-methylaniline

A solution of 200 g of 3-fluorotoluene and 670 ml of concentrated nitric acid was heated at 50°-55° for 8 hours; after standing overnight, the reaction mixture was poured into 1200 ml of ice-water. The organic layer was separated, and the aqueous layer was extracted three times with ether; the organic fraction and the ethereal extracts were combined, washed once with water and saturated sodium chloride solution. The combined organic fraction was dried over magnesium sulfate, filtered, and evaporated under reduced pressure to give a yellow oil. This crude product was distilled using a 30-cm vacuum-jacketed column filled with glass helices to yield 192.7 g of 5-fluoro-2-nitrotoluene, bp 74.5°-77°/4 mm.

A mixture of 125 g of 5-fluoro-2-nitrotoluene, 3.0 g of 5% palladium on carbon, and 200 ml of ethanol was reduced in a Parr hydrogenator under 46 p.s.i. hydrogen pressure. After hydrogen uptake had ceased, the catalyst was removed by filtration, and the ethanolic filtrate was evaporated under reduced pressure to give a colorless liquid. Purification by vacuum distillation yielded 85.7 g of 4-fluoro-2-methylaniline, b.p. 67°–71°/4.2 mm.

B. 4-Fluoro-2-methyl-N-(2,2,2-trifluoroethyl)aniline

To a solution of 86.0 g of 4-fluoro-2-methylaniline in 300 ml of benzene was added, dropwise over 0.5 hour, 145 g of trifluoroacetic anhydride, and the resulting mixture was refluxed for 5 hours. After being cooled, the reaction mixture was evaporated under reduced pressure to give a colorless liquid which crystallized upon standing. The white solid was triturated with cyclohexane, filtered, washed once with cold 1-chlorobutane, and dried to yield 80.1 g of 4-fluoro-2-methyl-2′,2′,2′-trifluoroacetanilide, m.p. 74°–77°.

A solution of 80.0 g of 4-fluoro-2methyl-2′,2′,2′-trifluoroacetanilide in 500 ml of anhydrous tetrahydrofuran was treated, dropwise at room temperature, with 600 ml of a 1.0 M solution of borane in tetrahydrofuran. The reaction was heated at reflux overnight, then cooled to $-5°$– $-10°$ (dry ice/acetone bath), and treated dropwise with 90 ml of 6N hydrochloric acid while maintaining the temperature below 0°. The organic solvent was removed by evaporation under reduced pressure, and the residue was dissolved in 500 ml of water and neutralized with 50% sodium hydroxide solution. The free amine was extracted with methylene chloride to yield, after drying (magnesium sulfate) and stripping, a colorless liquid. Purification by vacuum distillation gave 66.2 g. of 4-fluoro-2-methyl-N-(2,2,2-trifluoroethyl)aniline, b.p. 61°–63°/1 mm.

C. 6-Fluoro-1,4-dihydro-8-methyl-4-oxo-1-(2,2,2-trifluoroethyl)-3-quinolinecarboxylic Acid, Ethyl Ester A mixture of 66.1 g of 4-fluoro-2-methyl-N-(2,2,2-trifluoroethyl)aniline and 75.0 g of diethyl ethoxymethylenemalonate was heated at 160° for 20 hours. Eight hundred grams of polyphosphoric acid (ca. 400 ml) was added and the resulting mixture heated at 105°–115° for 20 minutes. The hot reaction mass was poured onto 1 kg of cracked ice to hydrolyze the polyphosphoric acid; the resulting solid was filtered and recrystallized from acetonitrile to yield 45.2 g of 6-fluoro-1,4-dihydro-8-methyl-4-oxo-1-(2,2,2-trifluoroethyl)-3-quinolinecarboxylic acid, ethyl ester, m.p. 154°–158°.

Using the appropriately-substituted 4-fluoro-N-(2,2,2-trifluoroethyl)aniline in place of 4-fluoro-2-methyl-N-(2,2,2-trifluoroethyl)aniline in the procedure of Example 1C, the following 3-quinolinecarboxylic acid, ethyl esters, can be prepared:

| | Starting aniline | Product | m.p. |
|---|---|---|---|
| a. | 4-fluoro-N-(2,2,2-trifluoroethyl)aniline (n=0) | 6-fluoro-1,4-dihydro-4-oxo-1-(2,2,2-trifluoroethyl)-3-quinolinecarboxylic acid, ethyl ester | 217°–218° |
| b. | 4-fluoro-3-methyl-N-(2,2,2-trifluoroethyl)-aniline (n=1) | 6-fluoro-1,4-dihydro-5-methyl-4-oxo-1-(2,2,2-trifluoroethyl)-3-quinolinecarboxylic acid, ethyl ester, and | 230°–231° |
| | | 6-fluoro-1,4-dihydro-7-methyl-4-oxo-1-(2,2,2-trifluoroethyl)-3-quinolinecarboxylic acid, ethyl ester | 202°–203° |
| c. | 4-fluoro-2,3-dimethyl-N-(2,2,2-trifluoroethyl)-aniline (n=2) | 6-fluoro-1,4-dihydro-7,8-dimethyl-4-oxo-1-(2,2,2-trifluoroethyl)-3-quinolinecarboxylic acid, ethyl ester | 168°–170° |

Using the appropriately-substituted difluoro-N-(2,2,2-trifluoroethyl)aniline in place of 4-fluoro-2-methyl-N-(2,2,2-trifluoroethyl)aniline in the procedure of Example 1C, the following 3-quinolinecarboxylic acid, ethyl ester can be prepared 6,8-difluoro-1,4-dihydro-4-oxo-1-(2,2,2-trifluoroethyl)-3-quinolinecarboxylic acid, ethyl ester m.p. 158–160.

EXAMPLE 2

6-Fluoro-1,4-dihydro-8-methyl-4-oxo-1-(2,2,2-trifluoroethyl)-3-quinolinecarboxylic Acid A mixture of 38.0 g of 6-fluoro-1,4-dihydro-8-methyl-4-oxo-1-(2,2,2-trifluoroethyl)-3-quinolinecarboxylic acid, ethyl ester and 800 ml of 6N hydrochloric acid was heated at reflux for 1.5 hours; the reaction mass was cooled, filtered, washed with water, and dried to give 36.4 g of 6-fluoro-1,4-dihydro-8-methyl-4-oxo-1-(2,2,2-trifluoroethyl)-3-quinolinecarboxylic acid, m.p. 221°–223°.

Using the procedure of Example 2 with the appropriately-substituted 3-quinolinecarboxylic acid esters, the following carboxylic acids can be prepared:
a. 6-fluoro-1,4-dihydro-4-oxo-1-(2,2,2-trifluoroethyl)-3-quinolinecarboxylic acid, m.p. 281°–282°
b. 6-fluoro-1,4-dihydro-5-methyl-4-oxo-1-(2,2,2-trifluoroethyl)-3-quinolinecarboxylic acid, m.p. 277°–278°
c. 6-fluoro-1,4-dihydro-7-methyl-4-oxo-1-(2,2,2-trifluoroethyl)-3-quinolinecarboxylic acid, m.p. 302°–303°
d. 6-fluoro-1,4-dihydro-7,8-dimethyl-4-oxo-1-(2,2,2-trifluoroethyl)-3-quinolinecarboxylic acid, m.p. 228°–229°
e. 6,8-difluoro-1,4-dihydro-4-oxo-1-(2,2,2-trifluoroethyl)-3-quinolinecarboxylic acid, m.p. 198°–201°

EXAMPLE 3

6-Fluoro1,4-dihydro-8-methyl-4-oxo-1-(2,2,2-trifluoroethyl)-3-quinolinecarboxylic Acid, Methyl Ester To a solution of 2.3 g of 6-fluoro-1,4-dihydro-8-methyl-4-oxo-1-(2,2,2-trifluoroethyl)-3-quinolinecarboxylic acid in 25 ml of pyridine, at 0°, was added 1.1 ml of thionyl chloride. The resulting slurry was stirred at room temperature for 0.5 hour and subsequently treated with 5 ml of methanol. After 1 hour, the reaction mixture was poured into 200 ml of water; the resulting white solid was filtered, washed with water, and dried to give 2.0 g of 6-fluoro-1,4-dihydro-8-methyl-4-oxo-1-(2,2,2-trifluoroethyl)-3-quinolinecarboxylic acid, methyl ester, m.p. 168°–171°.

EXAMPLE 4

6-Fluoro-1,4-dihydro-4-oxo-1-(2,2,2-trifluoroethyl)-3-quinolinecarboxylic Acid, (2,2,2-Dimethyl-1-oxopropoxymethyl)Ester To a mixture of 8.7 g of 6-fluoro-1,4-dihydro-4oxo-1-(2,2,2-trifluoroethyl)-3-quinolinecarboxylic acid, 4.3 g of potassium carbonate, and 100 ml dimethylformamide was added 10.0 g of chloromethyl pivalate. The reaction mixture was stirred overnight at room temperature and then poured into 250 ml of water; the resulting solid was collected by filtration, dried, and recrystallized from methylene chloride to give 6-fluoro-1,4-dihydro-4-oxo-1-(2,2,2-trifluoroethyl)-3-quinolinecarboxylic acid,(2,2,2-dimethyl-1-oxopropoxymethyl)ester, m.p. 192°–193°.

EXAMPLE 5

6-Fluoro-1,4-dihydro-8-methyl-4-oxo-1-(2,2,2-trifluoroethyl)-3-quinolinecarboxylic Acid, Sodium Salt To a solution of 0.6 g of 6-fluoro-1,4-dihydro-8-methyl-4-oxo-1-(2,2,2-trifluoroethyl)-3-quinolinecarboxylic acid in 75 ml of hot ethanol was added 2 ml of 1.0N sodium hydroxide solution. Evaporation under reduced pressure left a white solid, 6-fluoro-1,4-dihydro-8-methyl-4-oxo-1-(2,2,2-trifluoroethyl)-3-quinolinecarboxylic acid, sodium salt, m.p. 275°–276° (dec.).

Using a procedure similar to that of Example 5 with the appropriate 3-quinolinecarboxylic acid and inorganic hydroxide, amine, or ammonium hydroxide, the following salts can be prepared:

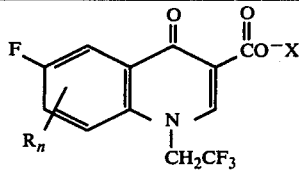

| Base | $R_n$ | X |
|---|---|---|
| a. KOH | H | $K^+$ |
| b. $NH_4OH$ | 7,8-$(CH_3)_2$ | $NH_4^+$ |
| c. $(CH_3CH_2)_3N$ | 7-$CH_3$ | $(CH_3CH_2)_3NH^+$ |
| d. $(CH_3CH_2CH_2CH_2)_4N^+OH^-$ | 8-$CH_3$ | $(CH_3CH_2CH_2CH_2)_4N^+$ |

By substituting the appropriate alcohol or thiol for methanol in the procedure of Example 3, the following ester and thiol ester derivatives are readily prepared:

FORMULATION

Useful information of these compounds can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at

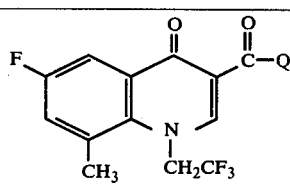

| Q—H | Q | m.p. |
|---|---|---|
| a. $(CH_3)_2CHOH$ | Q = $OCH(CH_3)_2$ | 144° – 147° |
| b. $CH_3(CH_2)_3OH$ | Q = $O(CH_2)_3CH_3$ | 96° – 106° |
| c. $CH_3SH$ | Q = $SCH_3$ | 203° – 205° |
| d. $(CH_3)_2CH—CH_2SH$ | Q = $SCH_2CH(CH_3)_2$ | |
| e. $CH_3(CH_2)_6CH_2OH$ | Q = $O(CH_2)_7CH_3$ | 73° – 76° | spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide," 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual," M. C. Publ. Corp., Ridgewood, N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," *Chemical Engineering*, Dec. 4, 1967, pp. 147ff. and "Perry's Chemical Engineer's Handbook," 4th. Edn., McGraw-Hill, New York, 1963, pp. 8–59ff.

For further information regarding the art of formulation, see for example:

J. B. Buchanan, U.S. Pat. No. 3,576,834, Apr. 27, 1971, Col. 5, Line 36 through Col. 7, Line 70 and Exs. 1–4, 17, 106, 123–140.

R. R. Shaffer, U.S. Pat. No. 3,560,616, Feb. 2, 1971, Col. 2, Line 48 through Col. 7, Line 26 and Examples 3–9, 11–18.

E. Somers, "Formulation," Chapter 6 in Torgeson, "Fungicides," Vol. I, Academic Press, New York, 1967.

EXAMPLE 6

| Wettable Powder | |
| --- | --- |
| 6-Fluoro-1,4-dihydro-4-oxo-1-(2,2,2-trifluoroethyl)-3-quinolinecarboxylic acid, 2,2-dimethyl-1-oxopropoxymethyl ester | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active ingredient practically all below 10 microns in diameter. The product is reblended before packaging.

EXAMPLE 7

| Oil Suspension | |
| --- | --- |
| 6-Fluoro-1,4-dihydro-8-methyl-4-oxo-1-(2,2,2-trifluoroethyl)-3-quinolinecarboxylic acid | 25% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 8

| Aqueous Suspension | |
| --- | --- |
| 6-Fluoro-1,4-dihydro-7,8-dimethyl-4-oxo-1-(2,2,2-trifluoroethyl)-3-quinolinecarboxylic acid | 25% |
| Hydrated attapulgite | 3% |
| Crude calcium ligninsulfonate | 10% |
| Sodium dihydrogen phosphate | 0.5% |
| Water | 61.5% |

The ingredients are ground together in a ball or roller mill until the solid particles have been reduced to diameters under 10 microns.

EXAMPLE 9

| Solution | |
| --- | --- |
| 6-Fluoro-1,4-dihydro-8-methyl-4-oxo-1-(2,2,2-trifluoroethyl)-3-quinolinecarboxylic acid, ethyl ester | 30% |
| Dimethylformamide | 70% |

The ingredients are combined and stirred to produce a solution, which can be used for low volume applications.

USE

The compounds of this invention possess outstanding bacterial activity when employed to prevent or mitigate damage to plants by bacteria. The compounds are particularly effective for the control of damage caused by pathogenic bacteria of the genus Erwinia. Plants and harvested plant products (potatoes and other vegetables) are protected from such devastating diseases as fire blight of apple or pear incited by *Erwinia amylovora*, soft rot of vegetables incited by *Erwinia caratovora*, and gall formation on both herbaceous and woody plants incited by *Agrobacterium tumefaciens*.

The compounds of this invention are especially suited for the protection of living plants. Rates of application to seeds, tubers, bulbs and other plant reproductive parts, range from 10 to 1000 parts per million (ppm) concentration in the dip suspension. The compounds may also be applied at a rate from 1 to 100 grams of active compound per kilogram of planting material. Applications are made from solutions, suspensions, slurries, or dusts.

Rates of application to foliage, stems and fruit of living plants range from 10 ppm to 1000 ppm in the spray or dip suspension, or from 0.1 to 10 kilograms of active ingredient per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications may need to be repeated one or many more times. Applications are made from solutions, suspensions, slurries, or dusts.

The compositions of the invention can contain, in addition to the active ingredient of this invention, conventional pesticides or other agricultural chemicals such as fruit-set or fruit-thinning agents, fertilizer ingredients and the like, so the compositions can serve other useful purposes in addition to the control of bacteria. The proper choice and amounts are readily made by one skilled in the art of protecting plants from pest depredations.

The outstanding control of bacterial diseases by the compounds of this invention is illustrated by a greenhouse experiment on apple seedlings inoculated with the bacterial pathogen, *Erwinia amylovora*, which incites the devastating fire blight disease, and a laboratory experiment for the control of bacterial soft rot of potatoes incited by *Erwinia caratovora*, and a greenhouse experiment on tomato seedlings inoculated with the bacterial pathogen, *Agrobacterium tumefaciens*, which incites galling.

EXAMPLE 10

The compounds listed in the table below were dissolved in acetone and suspended at the indicated concentrations in water containing 500 ppm of surfactant Trem 014. Apple seedlings about two weeks old were sprayed to the point of run-off with the chemical suspensions. One day after treatment the apple seedlings were inoculated by spraying them with a suspension of *Erwinia amylovora* bacteria, and incubated in a greenhouse for six days. The untreated check plants were severely blighted and a percent disease control rating was assigned to each treated plant. An average of the replicate plants is recorded on the following table.

| Compound | Percent Fire Blight Control | | | |
|---|---|---|---|---|
| | 200 ppm | 100 ppm | 50 ppm | 50 ppm |
| 6-Fluoro-1,4-dihydro-4-oxo-1-(2,2,2-trifluoroethyl)-3-quinolinecarboxylic acid, 2,2-dimethyl-1-oxopropoxymethyl ester. | 95 | 90 | 85 | 95 |
| 6-Fluoro-1,4-dihydro-8-methyl-4-oxo-1-(2,2,2-trifluoroethyl)-3-quinolinecarboxylic acid, ethyl ester | 97 | 86 | 85 | 87 |
| 6-Fluoro-1,4-dihydro-7,8-dimethyl-4-oxo-1-(2,2,2-trifluoroethyl)-3-quinolinecarboxylic acid, ethyl ester | 88 | 85 | 35 | — |
| 6-Fluoro-1,4-dihydro-8-methyl-4-oxo-1-(2,2,2-trifluoroethyl)-3-quinolinecarboxylic acid | 97 | 85 | 90 | 70 |
| 6-Fluoro-1,4-dihydro-7,8-dimethyl-4-oxo-1-(2,2,2-trifluoroethyl)-3-quinolinecarboxylic acid | 80 | 93 | 85 | 87 |
| 6-Fluoro-1,4-dihydro-8-methyl-4-oxo-1-(2,2,2-trifluoroethyl)-3-quinolinecarboxylic acid, methyl ester | 100 | 80 | 82 | 90 |
| 6-Fluoro-1,4-dihydro-8-methyl-4-oxo-1-(2,2,2-trifluoroethyl)-3-quinolinecarboxylic acid, (1-methylethyl)ester | 100 | 90 | 83 | 40 |
| 6,8-Difluoro-1,4-dihydro-4-oxo-1-(2,2,2-trifluoroethyl)-3-quinoline carboxylic acid, ethyl ester | 75 | 100 | | |
| Streptomycin (Agri-Strep®) | 90 | 84 | 70 | 0 |

| Compound | Percent Fire Blight Control | | |
|---|---|---|---|
| | 600 ppm | 200 ppm | 100 ppm |
| Compound of Gerster, U.S. Patent 3,924,042 | 30 | 10 | 0 |

EXAMPLE 11

The compounds listed in the table below were dissolved in acetone and suspended at a concentration of 200 ppm in water containing 500 ppm of surfactant Trem 014. Potato tuber pieces cut on two sides and about 5 mm thick were dipped into the suspensions for five minutes and then placed on moist paper for about four hours befoe inoculation. Tuber pieces were inoculated by placing two drops of a suspension of *Erwinia caratovora* bacteria on each piece and incubated at 33° C. in a saturated humidity chamber for two days. Untreated pieces were completely digested and a percent disease control rating was assigned to each treated tuber piece. An average of the replicate pieces is recorded in the following table.

| Compound | Percent Bacterial Soft Rot Control |
|---|---|
| 6-Fluoro-1,4-dihydro-4-oxo-1-(2,2,2-trifluoroethyl)-3-quinolinecarboxylic acid, 2,2-dimethyl-1-oxopropoxymethyl ester | 56 |
| 6-Fluoro-1,4-dihydro-8-methyl-4-oxo-1-(2,2,2-trifluoroethyl)-3-quinolinecarboxylic acid, ethyl ester | 67 |
| 6-Fluoro-1,4-dihydro-8-methyl-4-oxo-1-(2,2,2-trifluoroethyl)-3-quinolinecarboxylic acid | 100 |
| 6-Fluoro-1,4-dihydro-7,8-dimethyl-4-oxo-1-(2,2,2-trifluoroethyl)-3-quinolinecarboxylic acid | 100 |
| Streptomycin (Agri-Strep®) | 93 |

EXAMPLE 12

The compounds listed in the table below were dissolved in acetone and suspended at a concentration of 200 ppm in water containing 500 ppm of surfactant Trem 014. The stems of four week tomato seedlings were sprayed until thoroughly wet with the chemical suspensions. One day after treatment the stems of the tomato seedlings were inoculated by spraying them with a suspension of *Agrobacterium tumefaciens* bacteria, and incubated in a greenhouse for sixteen days. The untreated check plants were severely galled and a percent disease control rating was assigned to each treated plant. An average of the replicate plants is recorded in the following table.

| Compound | Percent Crown Gall Control |
|---|---|
| 6-Fluoro-1,4-dihydro-8-methyl-4-oxo-1-(2,2,2-trifluoroethyl)-3-quinolinecarboxylic acid, ethyl ester | 88 |
| 6-Fluoro-1,4-dihydro-8-methyl-4-oxo-1-(2,2,2-trifluoroethyl)-3-quinolinecarboxylic acid | 50 |
| 6-Fluoro-1,4-dihydro-8-methyl-4-oxo-1-(2,2,2-trifluoroethyl)-3-quinolinecarboxylic acid, methyl ester | 90 |
| 6-Fluoro-1,4-dihydro-8-methyl-4-oxo-1-(2,2,2-trifluoroethyl)-3-quinolinecarboxylic acid, (1-methylethyl)ester | 55 |
| 6,8-Difluoro-1,4-dihydro-oxo-1-(2,2,2-trifluoroethyl)-3-quinolinecarboxylic acid, ethyl ester | |
| Streptomycin (Agri-Strep®) | 0 |

"Consisting essentially of" is intended to have its customary meaning: namely, that all specified materials and conditions are very important in practicing the invention but that unspecified materials and conditions are not excluded so long as they do not prevent the benefits of the invention from being realized.

I claim:

1. A compound of the formula

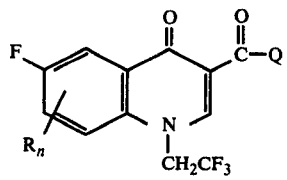

where
R = methyl or fluorine;
n = 0, 1, or 2;
Q = $OR_1$ or $SR_1$; and
$R_1$ = hydrogen, alkyl of 1-8 carbons, 2,2-dimethyl-1-oxopropoxymethyl, or horticulturally-suitable metal, amine, or ammonium salt;
provided when R is fluorine, n is 1.

2. A compound of claim 1 where n = 1 or 2.
3. A compound of claim 1 where Q = $OR_1$.
4. A compound of claim 1 where $R_1$ is alkyl of 1-4 carbons, 2,2-dimethyl-1-oxopropoxymethyl, or horticulturally-suitable metal, amine or ammonium salt.
5. A compound of claim 1 where n = 1 or 2, Q = $OR_1$ and $R_1$ is alkyl of 1-4 carbons, 2,2-dimethyl-1-oxopropoxymethyl, or horticulturally-suitable metal, amine or ammonium salt.
6. The compound of claim 1 which is 6-fluoro-1,4-dihydro-4-oxo-1-(2,2,2-trifluoroethyl)-3-quinolinecarboxylic acid,(2,2-dimethyl-1-oxopropoxymethyl) ester.
7. The compound of claim 1 which is 6-fluoro-1,4-dihydro-8-methyl-4-oxo-1-(2,2,2-trifluoroethyl)-3-quinolinecarboxylic acid, ethyl ester.
8. The compound of claim 1 which is 6-fluoro-1,4-dihydro-8-methyl-4-oxo-1-(2,2,2-trifluoroethyl)-3-quinolinecarboxylic acid.
9. The compound of claim 1 which is 6-fluoro-1,4-dihydro-7,8-dimethyl-4-oxo-1-(2,2,2-trifluoroethyl)-3-quinolinecarboxylic acid.
10. The compound of claim 1 which is 6,8-difluoro-1,4-dihydro-4-oxo-1-(2,2,2-trifluoroethyl)-3-quinolinecarboxylic acid.
11. The compound of claim 1 which is 6,8-difluoro-1,4-dihydro-4-oxo-1-(2,2,2-trifluoroethyl)-3-quinolinecarboxylic acid, ethyl ester.
12. A method of controlling bacterial plant disease which comprises applying to a plant to be protected an antibacterially effective amount of a compound of claim 1.
13. A method of controlling bacterial plant disease which comprises applying to a plant to be protected an antibacterially effective amount of a compound of claim 2.
14. A method of controlling bacterial plant disease which comprises applying to a plant to be protected an antibacterially effective amount of a compound of claim 3.
15. A method of controlling bacterial plant disease which comprises applying to a plant to be protected an antibacterially effective amount of a compound of claim 4.
16. A method of controlling bacterial plant disease which comprises applying to a plant to be protected an antibacterially effective amount of a compound of claim 5.
17. A method of controlling bacterial plant disease which comprises applying to a plant to be protected an antibacterially effective amount of the compound of claim 6.
18. A method of controlling bacterial plant disease which comprises applying to a plant to be protected an antibacterially effective amount of the compound of claim 7.
19. A method of controlling bacterial plant disease which comprises applying to a plant to be protected an antibacterially effective amount of the compound of claim 8.
20. A method of controlling bacterial plant disease which comprises applying to a plant to be protected an antibacterially effective amount of the compound of claim 9.
21. A method of controlling bacterial plant disease which comprises applying to a plant to be protected an antibacterially effective amount of the compound of claim 10.
22. A method of controlling bacterial plant disease which comprises applying to a plant to be protected an antibacterially effective amount of the compound of claim 11.
23. The method of claim 12 in which the bacteria is of the genus Erwinia.
24. The method of claim 23 in which the bacteria is *Erwinia amylovora.*
25. The method of claim 23 in which the bacteria is *Erwinia caratovora.*
26. The method of claim 12 in which the bacteria is *Agrobacterium tumefaciens.*
27. A composition for controlling bacterial plant disease consisting of an antibacterially effective amount of a compound of claim 1 and a carrier selected from the group consisting of a surfactant, solid diluent, liquid diluent and mixtures thereof.
28. A composition for controlling bacterial plant disease consisting of an antibacterially effective amount of a compound of claim 2 and a carrier selected from the group consisting of a surfactant, solid diluent, liquid diluent and mixtures thereof.
29. A composition for controlling bacterial plant disease consisting of an antibacterially effective amount of a compound of claim 3 and a carrier selected from the group consisting of a surfactant, solid diluent, liquid diluent and mixtures thereof.

30. A composition for controlling bacterial plant disease consisting of an antibacterially effective amount of a compound of claim 4 and a carrier selected from the group consisting of a surfactant, solid diluent, liquid diluent and mixtures thereof.

31. A composition for controlling bacterial plant disease consisting of an antibacterially effective amount of a compound of claim 5 and a carrier selected from the group consisting of a surfactant, solid diluent, liquid diluent and mixtures thereof.

32. A composition for controlling bacterial plant disease consisting of an antibacterially effective amount of a compound of claim 6 and a carrier selected from the group consisting of a surfactant, solid diluent, liquid diluent and mixtures thereof.

33. A composition for controlling bacterial plant disease consisting of an antibacterially effective amount of a compound of claim 7 and a carrier selected from the group consisting of a surfactant, solid diluent, liquid diluent and mixtures thereof.

34. A composition for controlling bacterial plant disease consisting of an antibacterially effective amount of a compound of claim 8 and a carrier selected from the group consisting of a surfactant, solid diluent, liquid diluent and mixtures thereof.

35. A composition for controlling bacterial plant disease consisting of an antibacterially effective amount of a compound of claim 9 and a carrier selected from the group consisting of a surfactant, solid diluent, liquid diluent and mixtures thereof.

36. A composition for controlling bacterial plant disease consisting of an antibacterially effective amount of a compound of claim 10 and a carrier selected from the group consisting of a surfactant, solid diluent, liquid diluent and mixtures thereof.

37. A composition for controlling bacterial plant disease consisting of an antibacterially effective amount of a compound of claim 11 and a carrier selected from the group consisting of a surfactant, solid diluent, liquid diluent and mixtures thereof.

* * * * *